(12) United States Patent
Müller et al.

(10) Patent No.: US 7,951,970 B2
(45) Date of Patent: May 31, 2011

(54) PROCESS FOR RECYCLING CYCLOPENTADIENYL DERIVATIVES AND PREPARING METALLOCENES FROM RECYCLED, SUBSTITUTED CYCLOPENTADIENYL DERIVATIVES

(75) Inventors: Patrik Müller, Frankfurt (DE); Robert L. Jones, Oakland, CA (US); Reynald Chevalier, Frankfurt (DE); Christian Sidot, Compiègne (FR); Valerie Garcia, Margny-les-Compiègne (FR)

(73) Assignee: Basell Polyolefine GmbH, Wesseling (DE)

( * ) Notice: Subject to any disclaimer, the term of this patent is extended or adjusted under 35 U.S.C. 154(b) by 408 days.

(21) Appl. No.: 12/086,711

(22) PCT Filed: Dec. 19, 2006

(86) PCT No.: PCT/EP2006/012234
§ 371 (c)(1),
(2), (4) Date: Jun. 18, 2008

(87) PCT Pub. No.: WO2007/071370
PCT Pub. Date: Jun. 28, 2007

(65) Prior Publication Data
US 2010/0274035 A1    Oct. 28, 2010

Related U.S. Application Data

(60) Provisional application No. 60/787,453, filed on Mar. 30, 2006.

(30) Foreign Application Priority Data

Dec. 20, 2005   (DE) .................. 10 2005 061 326

(51) Int. Cl.
C07F 7/00       (2006.01)
C07F 17/00      (2006.01)
C07C 7/12       (2006.01)
(52) U.S. Cl. .............. 556/466; 556/11; 556/12; 556/53; 585/825
(58) Field of Classification Search ............. 556/11, 556/12, 53, 466; 585/825
See application file for complete search history.

(56) References Cited

U.S. PATENT DOCUMENTS

| | | |
|---|---|---|
| 5,616,747 A | 4/1997 | Rohrmann et al. |
| 5,770,752 A | 6/1998 | Kaufmann et al. |
| 5,831,105 A | 11/1998 | Aulbach et al. |
| 6,255,506 B1 | 7/2001 | Küber et al. |

(Continued)

FOREIGN PATENT DOCUMENTS

WO   WO 02/096920 A1   12/2002

(Continued)

OTHER PUBLICATIONS

Ortega, et al., "Synthesis and Use of Reverse-Phase Silica Gel for HPLC in Undergraduate Chemistry", *J. Chem. Educ.* 1996, 73, A26.

*Primary Examiner* — Porfirio Nazario Gonzalez
(74) *Attorney, Agent, or Firm* — Dilworth IP, LLC

(57) ABSTRACT

The present invention relates to a process for recycling cyclopentadienyl derivatives of the formulae (I) and (I'), a process for preparing metallocenes of the formula (III) from cyclopentadienyl derivatives of the formulae (I) and (I') or from bridged biscyclopentadienyl derivatives of the formula (II), in which the cyclopentadienyl derivatives of the formulae (I), (I') or (II) which are used have been at least partly recovered and purified by means of liquid-solid chromatography, and the use of liquid-solid chromatography for purifying substituted, recovered cyclopentadienyl derivatives of the formulae (I), (I') or (II).

7 Claims, 1 Drawing Sheet

U.S. PATENT DOCUMENTS

Figure 1:
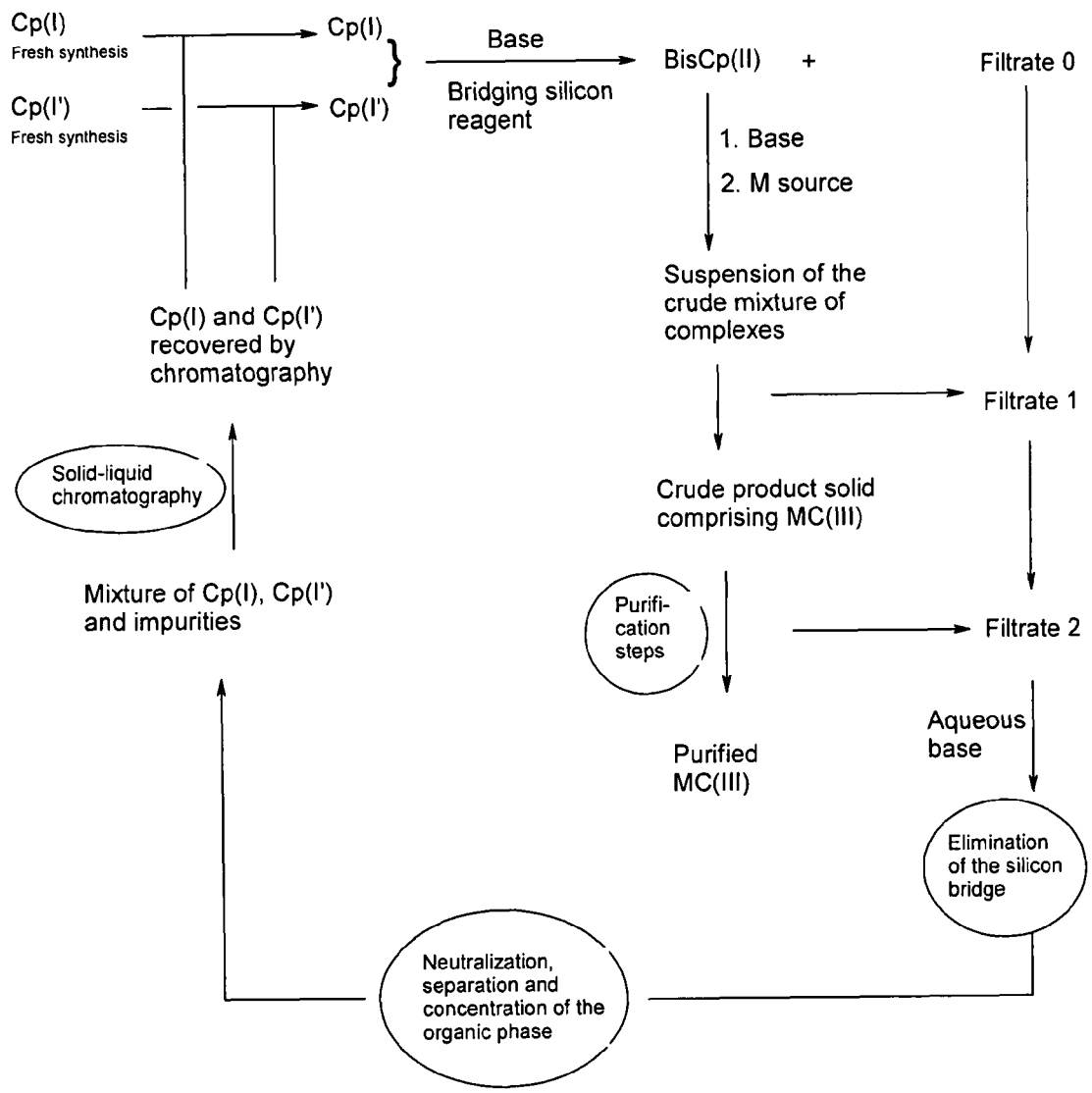

| | | |
|---|---|---|
| 6,262,286 B1 | 7/2001 | Gregorius et al. |
| 6,451,724 B1 | 9/2002 | Nifant'ev et al. |
| 6,930,190 B2 | 8/2005 | Nifant'ev et al. |
| 7,038,070 B2 | 5/2006 | Bingel et al. |
| 7,053,160 B1 | 5/2006 | Bingel et al. |
| 7,112,638 B2 | 9/2006 | Nifant'ev et al. |
| 7,141,637 B2 | 11/2006 | Elder et al. |
| 7,223,878 B2 | 5/2007 | Schulte et al. |
| 7,253,292 B2 | 8/2007 | Nifant'ev et al. |
| 7,342,078 B2 | 3/2008 | Schottek et al. |

FOREIGN PATENT DOCUMENTS

| | | |
|---|---|---|
| WO | WO 2005/108408 A2 | 11/2005 |

| Cp(I): | Cyclopentadienyl derivative of the formula (I) |
| Cp(I') | Cyclopentadienyl derivative of the formula (I') |
| BisCp(II) | Biscyclopentadienyl derivative of the formula (II) |
| MC(III) | Silicon-bridged metallocene of the formula (III) |
| M source | Transition metal compound having two leaving groups which can be replaced by cyclopentadienyl radicals |

PROCESS FOR RECYCLING CYCLOPENTADIENYL DERIVATIVES AND PREPARING METALLOCENES FROM RECYCLED, SUBSTITUTED CYCLOPENTADIENYL DERIVATIVES

CROSS-REFERENCE TO RELATED APPLICATIONS

This application is a national phase filing under 35 U.S.C. §371 of International Application PCT/EP2006/012234, filed 19 Dec. 2006, claiming priority to German Patent Application 102005061326.8 filed 20 Dec. 2005 and provisional U.S. Appl. No. 60/787,453 filed 30 Mar. 2006; the disclosures of International Application PCT/EP2006/012234, German Pat. Appl. 102005061326.8, and U.S. Appl. No. 60/787,453, each as filed, are incorporated herein by reference.

The present invention relates to a process for recycling cyclopentadienyl derivatives of the formulae (I) and (I'), a process for preparing metallocenes of the formula (III) from cyclopentadienyl derivatives of the formulae (I) and (I') or from bridged biscyclopentadienyl derivatives of the formula (II), in which the cyclopentadienyl derivatives of the formulae (I), (I') or (II) which are used have been at least partly recovered and purified by means of liquid-solid chromatography, and the use of liquid-solid chromatography for purifying substituted, recovered cyclopentadienyl derivatives of the formulae (I), (I') or (II).

In the past 15 years, research and development on the use of organic transition metal compounds, in particular metallocenes, as catalyst components for the polymerization and copolymerization of olefins has been pursued intensively in universities and in industry with the objective of preparing tailored polyolefins. Now, not only the ethylene-based polyolefins prepared by means of metallocene catalyst systems but also, in particular, the propylene-based polyolefins prepared by means of metallocene catalyst systems represent a dynamically growing market segment.

In the preparation of polyolefins, in particular in the preparation of isotactic polypropylenes, metallocenes whose substituted cyclopentadienyl ligands are prepared in a plurality of syntheses are used. The preparation of substituted cyclopentadienyl ligands is described, for example, in EP 0 576 970, WO 1998/40331, WO 1999/24446, WO 2001/47939, WO 2001/48034, WO 2002/092564, WO 2003/014107 or WO 2003/045964.

Metallocenes which are used for preparing isotactic polypropylenes are usually bridged racemic metallocenes having substituted cyclopentadienyl ligands prepared by a complicated synthesis. In the synthesis of racemic ansa-metallocenes, these are generally obtained together with the undesirable meso-metallocenes which usually have to be separated off, so that part of the costly ligand which has not been converted into the desired racemic metallocene is inevitably lost. To minimize the loss of the costly starting materials, various diastereoselective synthetic methods in which the proportion of the desired racemic metallocene is higher than the proportion of the undesirable meso form have been developed. Such racemoselective processes are described, for example, in WO 1999/15538 or WO 2005/108408.

WO 2002/96920 describes a process for purifying racemic metallocenes by removing the by-products formed in the preparative process, with at least part of the bridged biscyclopentadienyl ligand which has not been converted into the desired product being recovered from the filtrates by crystallization.

Despite the progress achieved to date in the optimization of the metallocene synthesis in respect of the yield of the desired metallocene based on the ligand precursors used, there continues to be a need to improve the economics of the metallocene syntheses.

It was therefore an object of the present invention to discover a broadly applicable process for preparing metallocenes which improves the economics of the preparative process compared to the prior art.

We have accordingly found a process for recycling substituted cyclopentadienyl derivatives of the formulae (I) and (I')

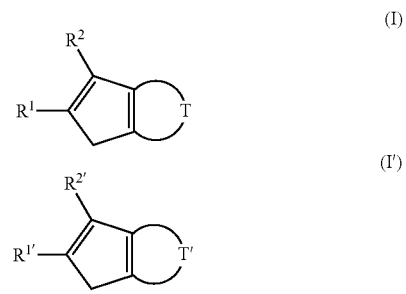

and/or their double bond isomers,
or bridged biscyclopentadienyl derivatives of the formula (II)

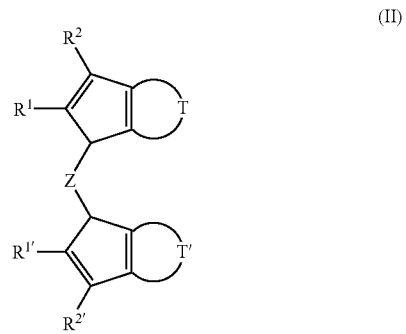

and/or their double bond isomers,
where
$R^1$, $R^{1'}$ are identical or different and are each an organic radical having from 1 to 40 carbon atoms,
$R^2$, $R^{2'}$ are identical or different and are each hydrogen or an organic radical having from 1 to 40 carbon atoms, or
$R^1$ with $R^2$ and/or $R^{1'}$ with $R^{2'}$ together with the atoms connecting them in each case form a monocyclic or polycyclic, saturated or unsaturated, substituted or unsubstituted ring system which has from 3 to 40 carbon atoms and has a ring size of from 5 to 12 atoms and may also comprise heteroatoms selected from the group consisting of the elements Si, Ge, N, P, As, Sb, O, S, Se or Te,
T, T' are identical or different and are each a divalent organic group which has from 1 to 40 carbon atoms and together with the cyclopentadienyl ring in each case forms at least one further saturated or unsaturated, substituted or unsubstituted ring system having a ring size of from 5 to 12 atoms, where T and T' within the ring system fused to the cyclopentadienyl ring may comprise the heteroatoms Si, Ge, N, P, As, Sb, O, S, Se or Te,
Z is a bridge between the two substituted cyclopentadienyl ligands which consists of a divalent atom or a divalent group, wherein the cyclopentadienyl derivatives of the formulae (I) and (I') and/or their double bond isomers or the bridged biscyclopentadienyl derivatives of the formula (II) and/or their double bond isomers which are used in the preparative process have been at least partly recovered from the filtrates, mother liquors, reaction residues and/or work-up residues obtained in the preparation of metallocenes and/or in the preparation of bridged biscyclopentadienyl ligands and subsequently purified by means of liquid-solid chromatography.

We further found a process for preparing metallocenes of the formula (III)

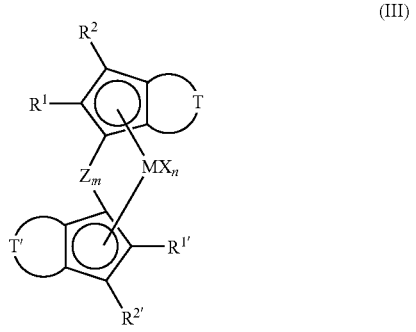

wherein
M is an element of group 3, 4, 5 or 6 of the Periodic Table of the Elements or the lanthanides,
the radicals X are identical or different and are each an organic or inorganic radical, with two radicals X also being able to be joined to one another,
n is 0, 1, 2 or 3, and
m is 0 or 1,
including the process for recycling substituted cyclopentadienyl derivatives of the formulae (I) and (I') and/or their double bond isomers, or bridged biscyclopentadienyl derivatives of the formula (II) and/or their double bond isomers, The radicals $R^1$ and $R^{1'}$ are identical or different, preferably different, and are each an organic radical having from 1 to 40 carbon atoms, for example $C_1$-$C_{40}$-alkyl, $C_1$-$C_{10}$-fluoroalkyl, $C_2$-$C_{40}$-alkenyl, $C_6$-$C_{40}$-aryl, $C_6$-$C_{10}$-fluoroaryl, arylalkyl, arylalkenyl or alkylaryl having from 1 to 10, preferably from 1 to 4, carbon atoms in the alkyl radical and from 6 to 22, preferably from 6 to 10, carbon atoms in the aryl radical, or a $C_2$-$C_{40}$-heteroaromatic radical which has at least one heteroatom selected from the group consisting of the elements O, N, S, P and Se, in particular O, N and S, and may be substituted by further radicals $R^3$, where $R^3$ is an organic radical having from 1 to 20 carbon atoms, for example $C_1$-$C_{10}$-, preferably $C_1$-$C_4$-alkyl, $C_6$-$C_{15}$-, preferably $C_6$-$C_{10}$-aryl, alkylaryl, arylalkyl, fluoroalkyl or fluoroaryl each having from 1 to 10, preferably from 1 to 4, carbon atoms in the alkyl radical and from 6 to 18, preferably from 6 to 10, carbon atoms in the aryl radical, and a plurality of radicals $R^3$ may be identical or different.

Preference is given to $R^1$ and $R^{1'}$ being identical or different, preferably different, and each being $C_1$-$C_{10}$-alkyl such as methyl, ethyl, n-propyl, isopropyl, n-butyl, i-butyl, s-butyl, t-butyl, n-pentyl, cyclopentyl, n-hexyl, cyclohexyl, n-heptyl or n-octyl, preferably methyl, ethyl or isopropyl.

The radicals $R^2$ and $R^{2'}$ are identical or different, preferably identical, and are each hydrogen or an organic radical having from 1 to 40 carbon atoms, for example $C_1$-$C_{40}$-alkyl, $C_1$-$C_{10}$-fluoroalkyl, $C_2$-$C_{40}$-alkenyl, $C_6$-$C_{40}$-aryl, $C_6$-$C_{10}$-fluoroaryl, arylalkyl, arylalkenyl or alkylaryl having from 1 to 10, preferably from 1 to 4, carbon atoms in the alkyl radical and from 6 to 22, preferably from 6 to 10, carbon atoms in the aryl radical, or a $C_2$-$C_{40}$-heteroaromatic radical which has at least one heteroatom selected from the group consisting of the elements O, N, S, P and Se, in particular O, N and S and may be substituted by further radicals $R^3$ as defined above and a plurality of radicals $R^3$ may be identical or different. $R^2$ and $R^{2'}$ are preferably hydrogen.

As an alternative, $R^1$ with $R^2$ and/or $R^{2'}$ with $R^{2'}$ together with the atoms connecting them in each case form a monocyclic or polycyclic, saturated or unsaturated, substituted or unsubstituted ring system which has from 3 to 40 carbon atoms and a ring size of from 5 to 12, in particular from 5 to 7, atoms and may also comprise heteroatoms selected from the group consisting of the elements Si, Ge, N, P, As, Sb, O, S, Se or Te, preferably Si, N, O or S, in particular S or N.

Examples of preferred, joined radicals $R^1/R^2$ and/or $R^{1'}/R^{2'}$ are

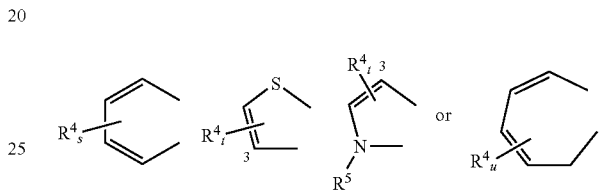

preferably

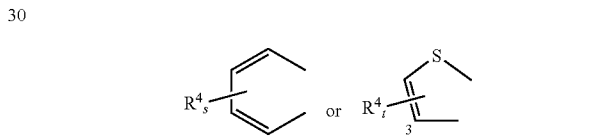

in particular

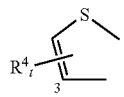

where
the radicals $R^4$ are identical or different and are each an organic radical having from 1 to 40, preferably from 1 to 20, carbon atoms, for example a cyclic, branched or unbranched $C_1$-$C_{20}$-, preferably $C_1$-$C_8$-alkyl radical, $C_2$-$C_{20}$-, preferably $C_2$-$C_8$-alkenyl radical, $C_6$-$C_{22}$-, preferably $C_6$-$C_{10}$-aryl radical, an alkylaryl or arylalkyl radical having from 1 to 10, preferably from 1 to 4, carbon atoms in the alkyl radical and from 6 to 22, preferably from 6 to 10, carbon atoms in the aryl radical, where the radicals may also be halogenated, or the radicals $R^4$ are substituted or unsubstituted, saturated or unsaturated, in particular aromatic heterocyclic radicals which have from 2 to 40, in particular from 4 to 20 carbon atoms and may comprise at least one heteroatom which is preferably selected from among the group of elements consisting of O, N, S and P, in particular O, N and S,
$R^5$ is hydrogen or is as defined for $R^4$,
or two adjacent radicals $R^4$ or $R^4$ with $R^5$ together with the atoms connecting them form a monocyclic or polycyclic, substituted or unsubstituted ring system which has from 3 to 40 carbon atoms and may also comprise heteroatoms selected from the group consisting of the elements Si, Ge, N, P, O, S, Se and Te, in particular N or S, the indices s are identical or different and are each a natural number from 0 to 4, in particular from 0 to 3, the indices t are identical or different and are each a natural number from 0 to 2, in particular 1 or 2, and the indices u are identical or different and are each a natural number from 0 to 6, in particular 1.

T and T' are identical or different, preferably identical, and are each a divalent organic group which has from 1 to 40 carbon atoms and together with the cyclopentadienyl ring forms at least one further saturated or unsaturated, substituted or unsubstituted ring system having a ring size of from 5 to 12, in particular from 5 to 7, atoms, with T and T' within the ring system fused to the cyclopentadienyl ring being able to comprise the heteroatoms Si, Ge, N, P, As, Sb, O, S, Se or Te, preferably Si, N, O or S, in particular S or N.

Examples of preferred divalent organic groups T or T' are

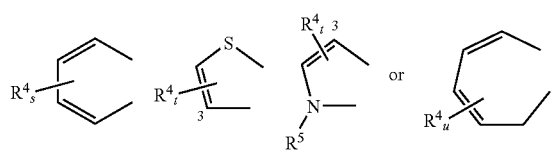

preferably

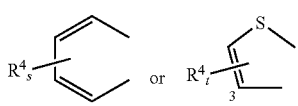

in particular

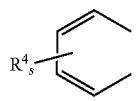

where $R^4$, $R^5$, s, t and u are as defined above.

Z is a bridge between the two substituted cyclopentadienyl rings which consists of a divalent atom or a divalent group. Examples of Z are:

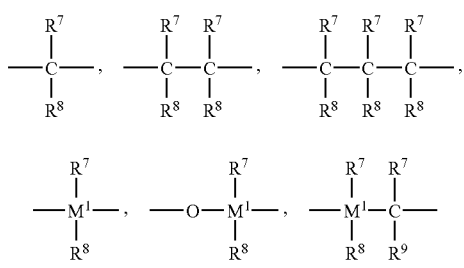

—B($R^7$)—, —B(N$R^7R^8$)—, —Al($R^7$)—, —O—, —S—, —S(O)—, —S((O)$_2$)—, —N($R^7$)—, —C(O)—, —P($R^7$)— or —P(O) ($R^7$)—, in particular

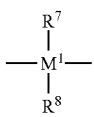

where $M^1$ is silicon, germanium or tin, preferably silicon or germanium, particularly preferably silicon, and $R^7$, $R^8$ and $R^9$ are identical or different and are each a hydrogen atom, a halogen atom, a trimethylsilyl group, a $C_1$-$C_{10}$-, preferably $C_1$-$C_3$-alkyl group, a $C_1$-$C_{10}$-fluoroalkyl group, a $C_6$-$C_{10}$-fluoroaryl group, a $C_6$-$C_{10}$-aryl group, a $C_1$-$C_{10}$-, preferably $C_1$-$C_3$-alkoxy group, a $C_7$-$C_{15}$-alkylaryloxy group, a $C_2$-$C_{10}$-, preferably $C_2$-$C_4$-alkenyl group, a $C_7$-$C_{40}$-arylalkyl group, a $C_8$-$C_{40}$-arylalkenyl group or a $C_7$-$C_{40}$-alkylaryl group or two adjacent radicals together with the atoms connecting them form a saturated or unsaturated ring having from 4 to 15 carbon atoms.

Preferred embodiments of Z are the bridges: dimethylsilanediyl, methylphenylsilanediyl, methyl-tert-butylsilanediyl, diphenylsilanediyl, dimethylgermanediyl, in particular dimethylsilanediyl.

M is an element of group 3, 4, 5 or 6 of the Periodic Table of the Elements or the lanthanides, preferably an element of group 4 of the Periodic Table of the Elements, e.g. titanium, zirconium or hafnium, particularly preferably zirconium or hafnium, in particular zirconium.

The radicals X are identical or different, preferably identical, and are each an organic or inorganic radical, with two radicals X also being able to be joined to one another. In particular, X is halogen, for example fluorine, chlorine, bromine, iodine, preferably chlorine, hydrogen, $C_1$-$C_{20}$-, preferably $C_1$-$C_4$-alkyl, $C_2$-$C_{20}$-, preferably $C_2$-$C_4$-alkenyl, $C_6$-$C_{22}$-, preferably $C_6$-$C_{10}$-aryl, an alkylaryl or arylalkyl group having from 1 to 10, preferably from 1 to 4, carbon atoms in the alkyl radical and from 6 to 22, preferably from 6 to 10, carbon atoms in the aryl radical, —O$R^d$ or —N$R^dR^e$, preferably —O$R^d$ or —NH$R^d$, with two radicals X also being able to be joined to one another, preferably two radicals —O$R^d$ which, in particular, form a substituted or unsubstituted 1,1'-di-2-phenoxide radical. Two radicals X can also form a substituted or unsubstituted diene ligand, in particular a 1,3-diene ligand. The radicals $R^d$ and $R^e$ are $C_1$-$C_{10}$-, preferably $C_1$-$C_4$-alkyl, $C_6$-$C_{15}$-, preferably $C_6$-$C_{10}$-aryl, alkylaryl, arylalkyl, fluoroalkyl or fluoroaryl each having from 1 to 10, preferably from 1 to 4, carbon atoms in the alkyl radical and from 6 to 22, preferably from 6 to 10, carbon atoms in the aryl radical and $R^e$ may also be hydrogen. Very particular preference is given to X being chlorine or methyl, in particular chlorine.

The index n is 0, 1, 2 or 3, with n+2 usually corresponding to the oxidation number of M, and in the case of the elements of group 4 of the Periodic Table of the Elements n is usually preferably 2. When M is chromium, n is preferably 0 or 1, in particular 0.

The index m is 0 or 1, preferably 1.

In the preparative process of the invention, use is made of cyclopentadienyl derivatives of the formulae (I) and (I') and/or their double bond isomers or bridged biscyclopentadienyl derivatives of the formula (II) and/or their double bond isomers, in particular cyclopentadienyl derivatives of the formulae (I) and (I') and/or their double bond isomers, which have been at least partly recovered from the filtrates, mother liquors, reaction residues and/or work-up residues obtained in the preparation of metallocenes and/or in the preparation of bridged biscyclopentadienyl ligands and subsequently purified by means of liquid-solid chromatography, with the proportion of recovered, i.e. recycled, cyclopentadienyl derivatives of the formulae (I) and (I') and/or their double bond isomers or bridged cyclopentadienyl derivatives of the formula (II) and/or their double bond isomers in the metallocene synthesis preferably being at least 5%, preferably at least 10%, particularly preferably at least 25%.

The cyclopentadienyl derivatives of the formulae (I) and (I') can have an identical or different substitution pattern in accordance with the above description. The process of the invention thus relates to the preparation of metallocenes having two identical cyclopentadienyl ligands or two different cyclopentadienyl ligands.

Furthermore, the substituents according to the present invention are, unless restricted further, defined as follows:

The term "organic radical having from 1 to 40 carbon atoms" as used in the present text refers to, for example, $C_1$-$C_{40}$-alkyl radicals, $C_1$-$C_{10}$-fluoroalkyl radicals, $C_1$-$C_{12}$-alkoxy radicals, saturated $C_3$-$C_{20}$-heterocyclic radicals, $C_8$-$C_{40}$-aryl radicals, $C_2$-$C_{40}$-heteroaromatic radicals, $C_8$-$C_{10}$-fluoroaryl radicals, $C_6$-$C_{10}$-aryloxy radicals, $C_3$-$C_{18}$-trialkylsilyl radicals, $C_2$-$C_{20}$-alkenyl radicals, $C_2$-$C_{20}$-alkynyl radicals, $C_2$-$C_{40}$-arylalkyl radicals or $C_8$-$C_{40}$-arylalkenyl radicals. An organic radical is in each case derived from an organic compound. Thus, the organic compound methanol can in principle give rise to three different organic radicals having one carbon atom, namely methyl ($H_3C$—), methoxy ($H_3C$—O—) and hydroxymethyl ($HOC(H_2)$—).

The term "alkyl" as used in the present text encompasses linear or singly or multiply branched saturated hydrocarbons which may also be cyclic. Preference is given to $C_1$-$C_{18}$-alkyl such as methyl, ethyl, n-propyl, n-butyl, n-pentyl, n-hexyl, n-heptyl, n-octyl, n-nonyl, n-decyl, cyclopentyl, cyclohexyl, isopropyl, isobutyl, isopentyl, isohexyl, sec-butyl or tert-butyl.

The term "alkenyl" as used in the present text encompasses linear or singly or multiply branched hydrocarbons having one or more C—C double bonds, which may be cumulated or alternating.

The term "saturated heterocyclic radical" as used in the present text refers to, for example, monocyclic or polycyclic, substituted or unsubstituted hydrocarbon radicals in which one or more carbon atoms, CH groups and/or $CH_2$ groups are replaced by heteroatoms preferably selected from the group consisting of O, S, N and P. Preferred examples of substituted or unsubstituted saturated heterocyclic radicals are pyrrolidinyl, imidazolidinyl, pyrazolidinyl, piperidyl, piperazinyl, morpholinyl, tetrahydrofuranyl, tetrahydropyranyl, tetrahydrothiophenyl and the like, and also methyl-, ethyl-, propyl-, isopropyl- and/or tert-butyl-substituted derivatives thereof.

The term "aryl" as used in the present text refers to, for example, aromatic and optionally also fused polyaromatic hydrocarbons which may be monosubstituted or polysubstituted by linear or branched $C_1$-$C_{18}$-alkyl, $C_1$-$C_{18}$-alkoxy, $C_2$-$C_{10}$-alkenyl or halogen, in particular fluorine. Preferred examples of substituted and unsubstituted aryl radicals are, in particular, phenyl, pentafluorophenyl, 4-methylphenyl, 4-ethylphenyl, 4-n-propylphenyl, 4-isopropylphenyl, 4-tert-butylphenyl, 4-methoxyphenyl, 1-naphthyl, 9-anthryl, 9-phenanthryl, 3,5-dimethylphenyl, 3,5-di-tert-butylphenyl or 4-trifluoromethylphenyl.

The term "heteroaromatic radical" as used in the present text refers to, for example, aromatic hydrocarbon radicals in which one or more carbon atoms are replaced by nitrogen, phosphorus, oxygen or sulfur atoms or combinations thereof. These may, like the aryl radicals, be monosubstituted or polysubstituted by linear or branched $C_1$-$C_{18}$-alkyl, $C_2$-$C_{10}$-alkenyl or halogen, in particular fluorine. Preferred examples are furyl, thienyl, pyrrolyl, pyridyl, pyrazolyl, imidazolyl, oxazolyl, thiazolyl, pyrimidinyl, pyrazinyl and the like, and also methyl-, ethyl-, propyl-, isopropyl- and/or tert-butyl-substituted derivatives thereof.

The term "arylalkyl" as used in the present text refers to, for example, aryl-comprising substituents whose aryl radical is linked via an alkyl chain to the corresponding remainder of the molecule. Preferred examples are benzyl, substituted benzyl, phenethyl, substituted phenethyl and the like.

The terms fluoroalkyl and fluoroaryl mean that at least one hydrogen atom, preferably more than one and a maximum of all hydrogen atoms, of the corresponding substituent have been replaced by fluorine atoms. Examples of fluorine-comprising substituents which are preferred according to the invention are trifluoromethyl, 2,2,2-trifluoroethyl, pentafluorophenyl, 4-trifluoromethylphenyl, 4-perfluoro-tert-butylphenyl and the like.

Preference is given to a process for preparing metallocenes of the formula (III) in which the metallocenes of the formula (III) are bridged, i.e. m=1, in particular silicon-bridged metallocenes of groups of 4 to 6, in particular group 4, of the Periodic Table of the Elements.

Particular preference is given to a process for preparing metallocenes of the formula (III) as described above in which two differently substituted cyclopentadienyl derivatives of the formulae (I) and (I') and/or their double bond isomers or a bridged biscyclopentadienyl derivative of the formula (II) and/or its double bond isomers having differently substituted cyclopentadienyl radicals are used.

The synthesis of the metallocenes of the formula (III) is known in principle and can be carried out, for example, by methods analogous to those described in EP 0 574 597 or EP 0 704 454.

It is usual to react a suitable transition metal source, e.g. zirconium tetrachloride, with the desired ligands, e.g. two equivalents of cyclopentadienyl ligand in the form of its lithium salt. To synthesize ansa-metallocenes, i.e. metallocenes having a bridged biscyclopentadienyl ligand, the desired cyclopentadienyl radicals are firstly joined to one another and subsequently reacted, usually after prior deprotonation, with the transition metal source. WO 2001/48034 and WO 2003/045964 describe, for example, the syntheses of bridged biscyclopentadienyl-metallocenes having two different cyclopentadienyl radicals of the formulae (I) and (I')

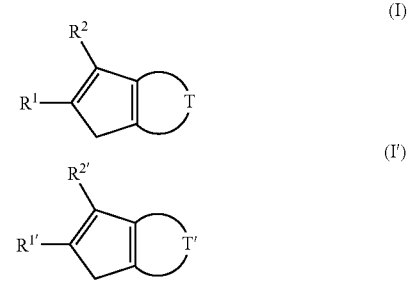

where the indices are as defined above.

The above-described synthesis scheme is illustrated by the following example, which does not, however, restrict the invention, of a metallocene of the formula (III) using two differently substituted cyclopentadienyl derivatives of the formulae (I) and (I') in the synthesis.

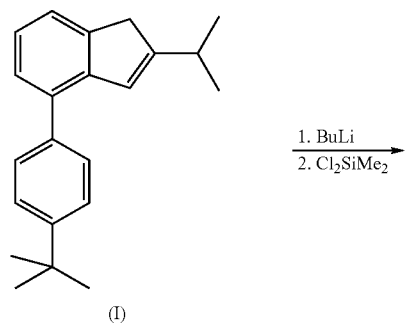

(I)

1. BuLi
2. Cl₂SiMe₂

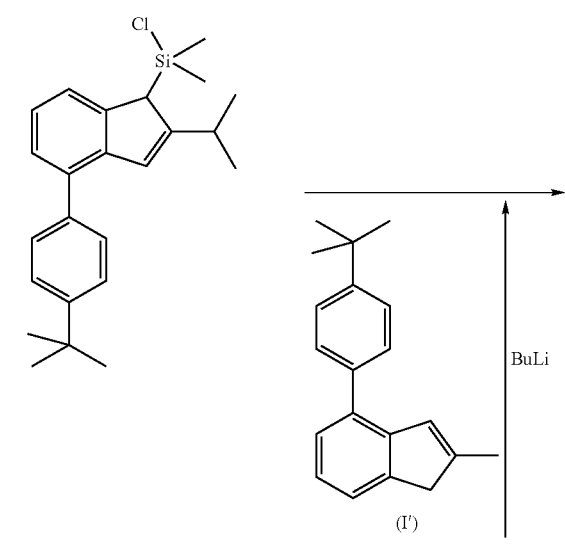

(I')

BuLi

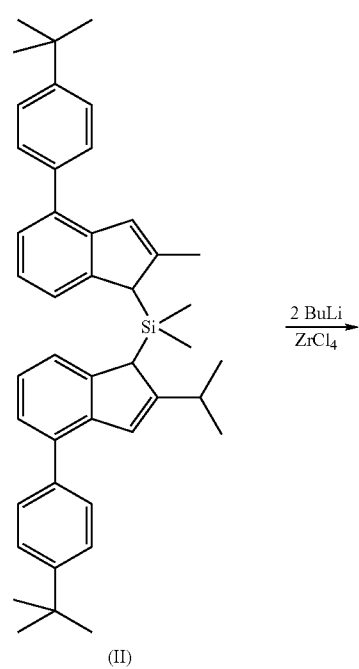

(II)

2 BuLi
ZrCl₄

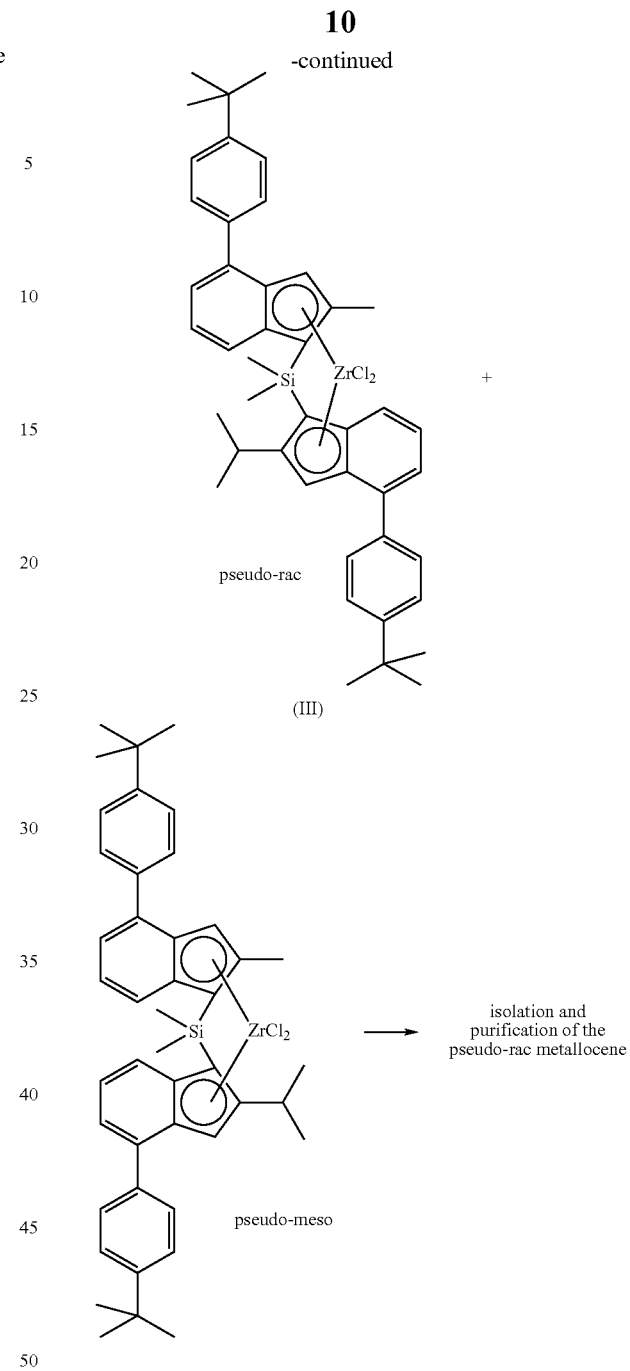

pseudo-rac (III)

pseudo-meso isolation and purification of the pseudo-rac metallocene

The process of the invention usually forms, as mentioned at the outset, not only the desired bridged rac-metallocenes of the formula (III) but also the corresponding meso compounds, with the terms meso and rac referring to the three-dimensional arrangement of the two cyclopentadienyl ring systems relative to one another. For example, in cases in which the two substituted cyclopentadienyl radicals on the bridge are not identical, there is no rac form having $C_2$ symmetry or meso form having $C_s$ symmetry, but instead there are only diastereomeric compounds having $C_1$ symmetry. When these different diastereomeric metallocene compounds which differ from one another in the three-dimensional arrangement of the differing substituents are used as catalyst component in the polymerization of propylene, they behave, purely on the basis of the three-dimensional arrangement of the two substituted cyclopentadienyl ligands relative to one another, like the $C_2$-symmetric rac isomer (isotactic polypropylene) or like the $C_s$-symmetric meso isomer (atactic polypropylene) of an ansa-metallocene having two identically substituted cyclopentadienyl ligands and can thus each be designated as a pseudo-rac form or a pseudo-meso form.

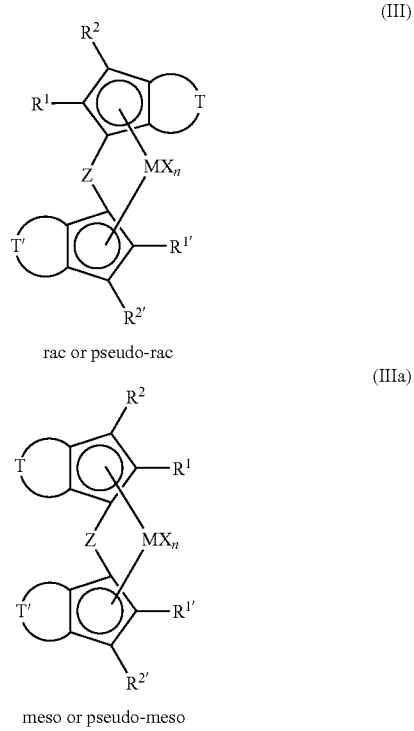

rac or pseudo-rac meso or pseudo-meso

In the following, rac and pseudo-rac form or meso and pseudo-meso form are distinguished only as rac and meso form.

The separation of the diastereomers, in particular the isolation and purification of the rac form, is known in principle.

In the synthesis of the bridged ligand system, in the preparation of the metallocene mixture and finally in the purification of the desired metallocene isomer, filtrates, mother liquors, reaction residues and/or work-up residues which comprise the cyclopentadienyl derivatives of the formulae (I) or (I') or bridged biscyclopentadienyl derivatives of the formula (II) are obtained. These fractions which comprise starting materials and/or intermediates and were hitherto usually disposed of are subjected, separately from one another or after having been combined and/or after further work-up steps such as a bridge elimination reaction, to liquid-solid chromatography in order to obtain purified cyclopentadienyl derivatives of the formulae (I), (I') and/or (II) or their double bond isomers which are subsequently reused in the process of the invention for preparing metallocenes.

The method of liquid-solid chromatography is known in principle. As stationary phase, it is possible to use both organic and inorganic finely divided solids such as aluminum oxides, silica gels, magnesium silicates, kieselguhr, activated carbon, cellulose, cellulose triacetate or silica gels modified with organic radicals, in particular hydrocarbon radicals, known as reversed phase materials. The choice of the solvents or solvent mixtures used as liquid mobile phase in the chromatographic method is known in principle to those skilled in the art and can be determined by means of a few routine thin-layer-chromatographic separation tests for the respective separation problem.

The stationary phase is usually introduced into separation columns, i.e. cylindrical vessels or tubes which frequently comprise glass or stainless steel and have openings at both end faces which usually have a smaller diameter than the internal diameter of the column itself. The mobile phase can flow through the solid phase under the action of gravity or with the aid of a deliberately generated superatmospheric pressure.

Very particular preference is given to a process for preparing metallocenes of the formula (III) as described above in which a reversed phase material is used as stationary phase in the chromatographic purification of the cyclopentadienyl derivatives of the formulae (I) and (I') and/or their double bond isomers or the bridged biscyclopentadienyl derivatives of the formula (II) and/or their double bond isomers, in particular in the purification of the cyclopentadienyl derivatives of the formulae (I) and (I') and/or their double bond isomers. Reversed phase materials are commercially available, for example LiChroprep RP-18-end-capped silica gels from Merck. Basic information on reversed phase silica gels is also given in J. Chem. Educ. 1996, 73, A26.

Special preference is given to a process for preparing metallocenes of the formula (III), in particular silicon-bridged metallocenes, as described above in which the cyclopentadienyl derivatives of the formulae (I) and (I') and/or their double bond isomers are recovered from the filtrates, mother liquors, reaction residues and/or work-up residues obtained in the preparation of metallocenes and/or in the preparation of bridged, in particular silicon-bridged biscyclopentadienyl ligands by subjecting these filtrates, mother liquors, reaction residues and/or work-up residues, either together or independently of one another, preferably together, to a single or multiple, acidic or basic, in particular basic, aqueous treatment in which any bonds present between bridging silicon atoms and cyclopentadienyl rings are cleaved, and subsequently isolating and if appropriate concentrating the organic phase comprising the cyclopentadienyl derivatives of the formulae (I) and (I') and/or their double bond isomers in order for them to be able to be purified further in the above-described liquid-solid chromatography.

FIG. 1 schematically shows an example of a preferred embodiment of the process of the invention for preparing bridged, in particular silicon-bridged, metallocenes of the formula (III), in particular from two differently substituted cyclopentadienyl derivatives of the formulae (I) and (I').

From cyclopentadienyl derivatives of the formulae (I) and (I'), with the two cyclopentadienyl derivatives being identical or different, in particular different, a silicon-bridged biscyclopentadienyl derivative of the formula (II) is prepared by known methods. For example, two equivalents of a cyclopentadienyl anion are reacted in a bridging reaction with an appropriate silicon-comprising bridging reagent, for example a diorganodichlorosilane such as dimethyldichlorosilane. As an alternative, the anion of a cyclopentadienyl derivative of the formula (I) is firstly reacted with an appropriate silicon-comprising bridging reagent, for example a diorganodichlorosilane such as dimethyldichlorosilane, to form a monocyclopentadienyl derivative which comprises a bridging group, for example a monochloromonocyclopentadienyldiorganosilane compound, and the second leaving group of the bridging group in this compound, for example the chlorine, is subsequently replaced by a further cyclopentadienyl radical which is generated by deprotonation of a cyclopentadienyl derivative of the formula (I') and can be different from the first cyclopentadienyl radical to give the desired uncharged bridged cyclopentadienyl compound of the formula (II). In the isolation and purification of the biscyclopentadienyl derivative of the formula (II), the filtrate 0 is usually obtained.

In the next step, the biscyclopentadienyl derivative of the formula (II) is usually doubly deprotonated by means of a strong base and subsequently reacted directly or after prior isolation with a suitable transition metal compound such as zirconium tetrachloride or one of the modified, rac-selective transition metal sources described in WO 1999/15538, WO 2000/31091 or WO 2005/108408 to give a metallocene of the formula (III).

Strong bases which can be used for deprotonating the cyclopentadienyl derivatives of the formulae (I) and (I') or the biscyclopentadienyl derivative of the formula (II) are, for example, organometallic compounds or metal hydrides, preferably compounds comprising an alkali metal or an alkaline earth metal. Preferred bases are organolithium or organomagnesium compounds such as methyllithium, n-butyllithium, sec-butyllithium n-butyl-n-octylmagnesium or dibutylmagnesium, in particular n-butyllithium or methyllithium.

The deprotonation of the cyclopentadienyl derivatives of the formulae (I) and (I') or the biscyclopentadienyl derivative of the formula (II) is usually carried out in the temperature range from −78° C. to 110° C., preferably from 0° C. to 80° C. and particularly preferably from 20° C. to 70° C. Suitable inert solvents in which the deprotonation of the cyclopentadienyl derivatives by means of strong bases can be carried out are aliphatic or aromatic hydrocarbons such as benzene, toluene, xylene, mesitylene, ethylbenzene, cumene, decalin, tetralin, pentane, hexane, cyclohexane, heptane or ethers such as diethyl ether, di-n-butyl ether, tert-butyl methyl ether (MTBE), tetrahydrofuran (THF), 1,2-dimethoxyethane (DME), anisole, triglyme, dioxane and also any mixtures of these. Preference is given to solvents or solvent mixtures in which the preparation of the metallocene complexes of the formula (III) can likewise be carried out directly. After the reaction of the biscyclopentadienyl bisanion with a transition metal compound bearing two leaving groups, for example zirconium tetrachloride, a suspension in which the metallocene of the formula (III) is present as a solid can be obtained directly, as described, for example, in EP 0 576 970 or EP 0 574 597. The product-comprising solid is then isolated by filtration and a further filtrate 1, which can be combined with the filtrate 0, is obtained.

In the further purification of the metallocene of the formula (III) by removal of salts such as lithium chloride or magnesium chloride and removal of undesirable metallocene isomers, in particular the meso form, further residues which are referred to as filtrate 2 are obtained. The purification is preferably carried out by a method as described in EP 0 780 396. As an alternative, the metallocene can be separated from the salt by extraction with an organic solvent, for example methylene chloride, and freed of further undesirable by-products by crystallization and be obtained in purified form. In all cases, filtrates are obtained in addition to the isolated metallocenes of the formula (III).

The filtrates 0, 1 and 2 are preferably combined and treated with aqueous acid or base, in particular aqueous base, to cleave the silicon-cyclopentadienyl carbon bond. The cleavage reaction is preferably carried out at a temperature of from 0° C. to 200° C., particularly preferably from 20° C. to 150° C., in particular from 50° C. to 110° C. The reaction can be carried out under atmospheric pressure or under superatmospheric pressure.

Suitable bases are, in particular, alkali metal hydroxide and alkaline earth metal hydroxides. Preference is given to using sodium hydroxide or potassium hydroxide, in particular sodium hydroxide. The addition of phase transfer catalysts such as tetraalkylammonium salts or crown ethers such as 18-crown-6 can help to accelerate the cleavage reaction.

The molar ratio of bridged ligand, in particular silicon-bridged ligand, to hydroxide is usually from 1:0.1 to 1:100, preferably from 1:1 to 1:20, in particular from 1:2 to 1:10.

The presence of various organic solvents in the reaction mixture is unproblematical, as long as these solvents are inert toward the reactants and the desired products, for example the cyclopentadienyl derivatives of the formulae (I) and (I'), under the reaction conditions.

After carrying out the cleavage reaction, the reaction mixture is neutralized or made slightly acidic, the aqueous phase is separated off and discarded and the organic phase, which comprises cyclopentadienyl derivatives of the formulae (I) and (I'), is dried if appropriate, for example by means of magnesium sulfate, and subsequently concentrated to the extent necessary for the subsequent chromatographic purification. The chromatography is, as described above, a solid-liquid chromatography.

The purified, recovered cyclopentadienyl derivatives of the formulae (I) and (I') are finally reused together with the appropriate, necessary amounts of freshly prepared cyclopentadienyl derivatives of the formulae (I) and (I') in the renewed preparation of a metallocene of the formula (III).

The present invention further provides a process for recovering cyclopentadienyl derivatives of the formula (I) and/or their double bond isomers, as described above, from the filtrates, mother liquors, reaction residues and/or work-up residues obtained in the preparation of silicon-bridged metallocenes and/or in the preparation of silicon-bridged biscyclopentadienyl ligands using such cyclopentadienyl derivatives, wherein these filtrates, mother liquors, reaction residues and/or work-up residues, either together or independently of one another, preferably together, are subjected to a single or multiple, acidic or basic, in particular basic, aqueous treatment in which bonds between bridging silicon atoms and cyclopentadienyl rings are cleaved, and subsequently isolating and if appropriate concentrating the organic phase comprising the cyclopentadienyl derivatives of the formulae (I) and (I') and/or their double bond isomers in order for them to be able to be purified further in liquid-solid chromatography.

The present invention further provides for the use of recycled, substituted cyclopentadienyl derivatives of the formulae (I) and (I') and/or their double bond isomers or bridged biscyclo-pentadienyl derivatives of the formula (II) and/or their double bond isomers, as described above, which have been purified by means of liquid-solid chromatography in the synthesis of metallocenes, in particular metallocenes of the formula (III), wherein the substituted cyclo-pentadienyl derivatives are recovered from the filtrates, mother liquors, reaction residues and/or work-up residues obtained in the preparation of metallocenes and/or in the preparation of bridged biscyclopentadienyl ligands.

The present invention likewise provides for the use of liquid-solid chromatography, in particular liquid-solid chromatography using reversed phase materials as stationary phase, for purifying substituted cyclopentadienyl derivatives of the formulae (I) and (I') and/or their double bond isomers or bridged biscyclopentadienyl derivatives of the formula (II) and/or their double bond isomers, as described above, for preparing metallocenes, in particular metallocenes of the formula (III), wherein the substituted cyclopentadienyl derivatives to be purified are recovered from the filtrates, mother liquors, reaction residues and/or work-up residues obtained in the preparation of metallocenes and/or in the preparation of bridged biscyclopentadienyl ligands.

The metallocenes of the formula (III) prepared by the process of the invention can be used together with suitable cocatalysts and, if appropriate, suitable support materials as constituent of a catalyst system for the polymerization of olefins.

The invention is illustrated by the following examples which do not, however, restrict the scope of the invention.

EXAMPLES

General

The synthesis and handling of organometallic compounds was carried out with exclusion of air and moisture under argon (glove box and Schlenk technique).

2-isopropyl-4-(4'-tert-butylphenyl)-1-indene and 2-methyl-4-(4'-tert-butylphenyl)-1-indene were prepared by methods analogous to those described in WO 9840331 and WO 0148034.

Example 1

Synthesis of dimethylsilanediyl(2-methyl-4-(4'-tert-butylphenyl)-1-indene)(2-isopropyl-4-(4'-tert-butylphenyl)-1-indene) (1)

a) Preparation of 2-isopropyl-4-(4'-tert-butylphenyl)-1-indenyldimethylchlorosilane (1a)

7.4 ml (61 mmol) of dimethyldichlorosilane (DMDCS) were added at −40° C. to a solution of 2-isopropyl-4-(4'-tert-butylphenyl)indenyllithium which had been obtained by reacting 5.84 g (20.1 mmol) of 2-isopropyl-4-(4'-tert-butylphenyl)-1-indene dissolved in 50 ml of toluene and 2.57 ml (40 mmol) of tetrahydrofuran (THF) with 8.65 ml (23.1 mmol) of n-butyllithium (2.68 M in toluene). The reaction mixture was stirred overnight at room temperature. Excess DMDCS and THF were subsequently distilled off under reduced pressure and lithium chloride was filtered off with the aid of a glass filter frit. This gave 7.7 g (20.1 mmol) of (1a) in 20 g of toluene.

b) Preparation of 2-dimethylsilanediyl(2-methyl-4-(4'-tert-butylphenyl)-1-indene)(2-isopropyl-4-(4'-tert-butylphenyl)-1-indene)(1)

4.85 g (18.5 mmol) of 2-methyl-4-(4'-tert-butylphenyl)-1-indene dissolved in 45 g of toluene and 3 ml (37 mmol) of THF were deprotonated by means of 6.93 ml (18.5 mmol) of n-butyllithium (2.68 M in toluene) at 45° C. The reaction mixture was stirred at 45° C. for 1 hour, and the solution of 7.7 g (20.1 mmol) of (1a) in 20 g of toluene prepared in example 1a) was subsequently added. The reaction mixture was stirred at 60° C. for 3 hours and quenched by addition of 100 g of water. After a customary work-up, the organic phase was evaporated under reduced pressure and the oil obtained (12 g, mixture of ligand (1), the two indenes used and some impurities) was crystallized after addition of 30 g of methanol with vigorous stirring. Filtration, washing of the filter cake with a little methanol and drying gave 7.2 g of (1) (yield: 65%). The filtrate was partly evaporated and cooled to 0° C. After filtration, a second crystal fraction of the ligand (1) (0.9 g) was isolated (total yield: 72%).

The methanol-comprising filtrate (15 g of filtrate 0) was used as shown in the scheme of FIG. 1 for the "neutralization" of the filtrate 1 obtained in the preparation of the crude metallocene product.

HPLC analysis of filtrate 0 indicated the following composition:

| | | |
|---|---|---|
| 2-Methyl-4-(4'-tert-butylphenyl)-1-indene = | 5.6% by weight → | 0.84 g (3.2 mmol) |
| 2-Isopropyl-4-(4'-tert-butylphenyl)-1-indene = | 9.7% by weight → | 1.45 g (5 mmol) |
| Ligand (1) = | 5% by weight → | 0.75 g (1.23 mmol) |

Example 2

Synthesis of rac-dimethylsilanediyl(2-methyl-4-(4'-tert-butylphenyl)-1-indenyl)(2-isopropyl-4-(4'-tert-butylphenyl)-1-indenyl)zirconium dichloride (2)

a) Preparation of the Mixture of Rac/Meso Complexes (2a)

8.32 g (26 mmol) of n-butyllithium (20% by weight in toluene) were added at room temperature to a solution of 8.0 g (13.1 mmol) of ligand (1) in 100 g of toluene and 4.5 g of THF under protective gas (nitrogen atmosphere). The reaction mixture was stirred at 80° C. for 2 hours and subsequently cooled to 25° C. A suspension of 3.33 g (14.3 mmol) of zirconium tetrachloride in 6 g of toluene was added to this solution of the deprotonated ligand (1). This resulted in the temperature rising to 45° C. The reaction mixture was stirred at 45° C. for 2 hours, and after the suspension formed had been cooled to room temperature, the suspension was filtered through an invertible glass frit filter. The filter cake, a mixture of lithium chloride and metallocene, was washed twice with a total of 10 g of toluene.

The filtrate was evaporated to a volume of about 25 ml at about 48° C. under reduced pressure. A second fraction of metallocene crystallized from the solution. After filtration and washing of the second fraction with 4 g of toluene, the two isolated fractions of the metallocene were combined and dried under reduced pressure. The total yield of metallocene-comprising crude product (2a) was 8.1 g.

The methanol-comprising filtrate 0 from example 1 was combined with the filtrates from example 2a) (filtrate 1), resulting in any residual butyllithium present in filtrate 1 being destroyed.

b) Purification of (2a) to give rac-dimethylsilanediyl(2-methyl-4-(4'-tert-butylphenyl)-1-indenyl)(2-isopropyl-4-(4'-tert-butylphenyl)-1-indenyl)zirconium dichloride (2)

8.1 g of crude product (2a) were suspended in a solvent mixture comprising 64.31 g of acetone, 17.66 g of water, 0.49 g of THF and 8.75 g of toluene at 15° C. and after 5 minutes the rac/meso ratio was determined at this point in time by means of $^1$H-NMR. The suspension was subsequently heated to 20° C. and the change in the rac/meso ratio was monitored by means of $^1$H-NMR spectroscopy. After 2.5 hours at 20° C., the rac/meso ratio was greater than 20. The suspension was filtered through an invertible glass frit filter. The filter cake was washed four times with a total of 15 g of toluene and dried in a stream of nitrogen.

The isolated metallocene was suspended in 25 g of toluene at 25° C. and after stirring for two hours was isolated again by filtration and drying under reduced pressure. The yield of pure metallocene (2) was 2.3 g (22.8%).

All filtrates obtained in example 2b) were combined to form filtrate 2 (see FIG. 1). 190 g of filtrate 2 were obtained.

Example 3

Work-Up of the Combined Filtrates 2.62 g (65.5 mmol) of sodium hydroxide powder were added to the combined filtrates (filtrate 0, filtrate 1 and filtrate 2) from examples 1, 2a and 2b. The reaction mixture was refluxed for 3 hours. The reaction mixture was subsequently acidified with 50.4 g of 20% aqueous sulfuric acid (102.8 mmol). After phase separation, the organic phase was washed with 40 g of water, dried over magnesium sulfate and subsequently concentrated. This gave 9.2 g of a viscous oil.

| HPLC analysis: | 2-methyl-4-(4'-tert-butylphenyl)-1-indene: | 40.2% => 3.7 g (14.1 mmol) |
|---|---|---|
| | 2-isopropyl-4-(4'-tert-butylphenyl)-1-indene | 49.5% => 4.55 g (15.7 mmol) |

The viscous oil was fractionated by means of preparative HPLC (reversed phase chromatography column; 120 g of C18-end-capped SiO$_2$; acetonitrile/water (80/20); gradientless (isocratic) elution conditions; UV detector (235 nm)).

Three fractions were collected:
1) pure 2-methyl-4-(4'-tert-butylphenyl)-1-indene
2) mixture of the indenes
3) pure 2-isopropyl-4-(4'-tert-butylphenyl)-1-indene Removal of the solvents gave 2.73 g of pure 2-methyl-4-(4'-tert-butylphenyl)-1-indene (74%), 2.5 g of pure 2-isopropyl-4-(4'-tert-butylphenyl)-1-indene (55%) and 3.5 g of the mixed fraction comprising about 30% of 2-methyl-4-(4'-tert-butylphenyl)-1-indene and about 70% of 2-isopropyl-4-(4'-tert-butylphenyl)-1-indene. The recovered pure indenes were used for the renewed preparation of the bridged ligand (1) in a manner analogous to example 1.

Example 4

Synthesis of dimethylsilanediyl(2-methyl-4-(4'-tert-butylphenyl)-1-indene) (2-isopropyl-4-(4'-tert-butylphenyl)-1-indene) (1) Using the Indenes Recovered in Example 3

Using a method analogous to example 1, ligand (1) was prepared from 5.85 g of 2-isopropyl-4-(4'-tert-butylphenyl)-1-indene (2.4 g of recovered indene from example 3 and 3.45 g of indene from a fresh synthesis) and 4.85 g of 2-methyl-4-(4'-tert-butylphenyl)-1-indene (2.25 g of recovered indene from example 3 and 2.6 g of indene from a fresh synthesis). Work-up and crystallization gave 8.2 g of ligand (1).

The invention claimed is:

1. A process for recycling metallocene catalyst components, comprising:
   (a) recovering a cyclopentadienyl or a bridged biscyclopentadienyl derivative from a filtrate, mother liquor, reaction residue, and/or a work-up residue obtained in the preparation of a metallocenes and/or in the preparation of a bridged biscyclopentadienyl ligand; and
   (b) purifying the recovered derivative by liquid-solid chromatography;
   wherein the cyclopentadienyl derivatives are recovered from the filtrates, mother liquors, reaction residues and/or work-up residues obtained in the preparation of metallocenes and/or in the preparation of bridged biscyclopentadienyl ligands by subjecting these filtrates, mother liquors, reaction residues and/or work-up residues, either together or independently of one another, to a single or multiple, acidic or basic aqueous treatment in which any bonds present between bridging silicon atoms and cyclopentadienyl rings are cleaved, and subsequently isolating and, optionally, concentrating the organic phase comprising the cyclopentadienyl derivatives in order for them to be able to be purified further in the liquid-solid chromatography.

2. The process of claim 1 wherein the recovered derivative is used to prepare a metallocene.

3. The process of claim 1 wherein the filtrates, mother liquors, reaction residues and/or work-up residues containing a mixture of two differently substituted cyclopentadienyl derivatives or a bridged biscyclopentadienyl derivative having differently substituted cyclopentadienyl radicals are used in step (a).

4. The process of claim 1 wherein a reversed phase material is used as stationary phase in the chromatographic purification of the cyclopentadienyl or bridged biscyclopentadienyl derivatives.

5. The process of claim 1 wherein the cyclopentadienyl derivative has the formulae (I) or (I')

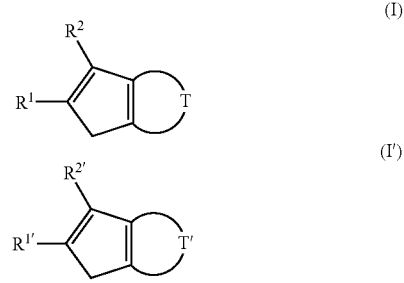

or the bridged biscyclopentadienyl derivative has the formula (II)

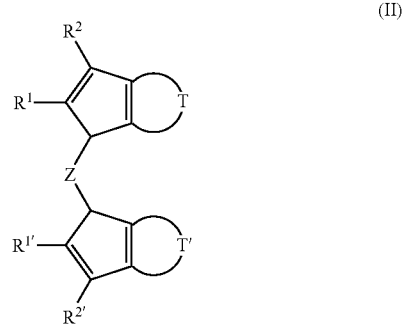

where
R¹, R¹' are identical or different and are each an organic radical having from 1 to 40 carbon atoms,
R², R²' are identical or different and are each hydrogen or an organic radical having from 1 to 40 carbon atoms, or R¹ with R² and/or R¹' with R²' together with the atoms connecting them in each case form a monocyclic or polycyclic, saturated or unsaturated, substituted or unsubstituted ring system which has from 3 to 40 carbon atoms and has a ring size of from 5 to 12 atoms and may also comprise heteroatoms selected from the group consisting of the elements, Si, Ge, N, P, As, Sb, 0, S, Se or Te,
T, T' are identical or different and are each a divalent organic group which has from 1 to 40 carbon atoms and together with the cyclopentadienyl ring in each case forms at least one further saturated or unsaturated, substituted or unsubstituted ring system having a ring size of from 5 to 12 atoms, where T and T' within the ring system fused to the cyclopentadienyl ring may comprise the heteroatoms Si, Ge, N, P, As, Sb, O, S, Se or Te, and
Z is a bridge between the two substituted cyclopentadienyl ligands which consists of a divalent atom or a divalent group.

6. The process of claim 1 wherein one or more of the products isolated from the liquid-solid chromatography are used to prepare a metallocene of the formula (III)

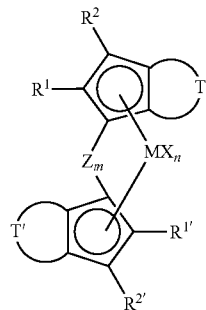
(III)

wherein
M is Group 3, 4, 5 or 6 element,
the radicals X are identical or different and are each an organic or inorganic radical, with two radicals X also being able to be joined to one another,
n is 0, 1, 2 or 3, and
m is 0 or 1.

7. The process of claim 6, wherein the metallocene is a silicon-bridged Group 4 to 6 metallocene.

* * * * *